(12) United States Patent
Mizuno et al.

(10) Patent No.: US 10,321,103 B2
(45) Date of Patent: Jun. 11, 2019

(54) IMAGE PICKUP SYSTEM AND IMAGE PROCESSING APPARATUS

(71) Applicant: OLYMPUS CORPORATION, Tokyo (JP)

(72) Inventors: Kyosuke Mizuno, Hino (JP); Ryuichi Yamazaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 270 days.

(21) Appl. No.: 15/450,146

(22) Filed: Mar. 6, 2017

(65) Prior Publication Data

US 2017/0180682 A1    Jun. 22, 2017

Related U.S. Application Data

(63) Continuation of application No. PCT/JP2015/078913, filed on Oct. 13, 2015.

(30) Foreign Application Priority Data

Nov. 7, 2014  (JP) ................................ 2014-227183

(51) Int. Cl.
    *H04N 7/18*     (2006.01)
    *H04N 5/04*     (2006.01)
    (Continued)

(52) U.S. Cl.
    CPC ......... *H04N 9/045* (2013.01); *A61B 1/00009* (2013.01); *A61B 1/00045* (2013.01);
    (Continued)

(58) Field of Classification Search
    None
    See application file for complete search history.

(56) References Cited

U.S. PATENT DOCUMENTS

| 4,746,972 A | * | 5/1988 | Takanashi | ............ | H04N 3/1525 |
| | | | | | 257/231 |
| 8,000,776 B2 | * | 8/2011 | Gono | ................. | A61B 1/00009 |
| | | | | | 600/109 |

(Continued)

FOREIGN PATENT DOCUMENTS

| JP | 2006-020788 A | | 1/2006 |
| JP | 2006020788 | * | 1/2006 |

(Continued)

OTHER PUBLICATIONS

Translation of JP2006020788.*

(Continued)

*Primary Examiner* — Mohammed S Rahaman
(74) *Attorney, Agent, or Firm* — Scully, Scott, Murphy & Presser, P.C.

(57) ABSTRACT

An image pickup system includes: a light source portion configured to sequentially emit first illumination light and second illumination light; an image pickup portion configured to perform image pickup of return light from an object; an image generating portion configured to generate a first image corresponding to return light of the first illumination light and a second image corresponding to return light of the second illumination light, each of which corresponds to one field, and sequentially output the first image and the second image; a synchronization processing portion configured to simultaneously output images corresponding to a plurality of fields, selectively assigning the images to three channels of a display apparatus; and a control portion configured to set image assignment to and image update frequency for the three channels based on an evaluation value acquired from the images generated by the image generating portion.

9 Claims, 5 Drawing Sheets

(51) Int. Cl.
    *H04N 9/04*         (2006.01)
    *A61B 1/04*         (2006.01)
    *A61B 1/06*         (2006.01)
    *G02B 23/24*       (2006.01)
    *G02B 23/26*       (2006.01)
    *A61B 1/00*         (2006.01)
    *H04N 5/217*       (2011.01)
    *H04N 5/225*       (2006.01)
    *H04N 9/76*         (2006.01)

(52) U.S. Cl.
    CPC ............... *A61B 1/04* (2013.01); *A61B 1/06* (2013.01); *A61B 1/0638* (2013.01); *G02B 23/24* (2013.01); *G02B 23/26* (2013.01); *H04N 5/04* (2013.01); *H04N 5/2173* (2013.01); *H04N 5/2256* (2013.01); *H04N 7/18* (2013.01); *H04N 9/76* (2013.01); *H04N 2005/2255* (2013.01); *H04N 2209/044* (2013.01)

(56) References Cited

U.S. PATENT DOCUMENTS

| | | |
|---|---|---|
| 2002/0008712 A1 | 1/2002 | Shigeta |
| 2008/0039686 A1* | 2/2008 | Mori ............... A61B 1/00165 600/109 |
| 2009/0041319 A1 | 2/2009 | Yamazaki et al. |
| 2010/0217077 A1* | 8/2010 | Gono ............... A61B 1/00096 600/109 |

FOREIGN PATENT DOCUMENTS

| | | |
|---|---|---|
| JP | 4884574 B2 | 2/2012 |
| WO | 2007/123028 A1 | 11/2007 |

OTHER PUBLICATIONS

Extended Supplementary European Search Report dated Apr. 4, 2018 in European Patent Application No. 15 85 6393.2.
International Search Report dated Jan. 19, 2016 issued in PCT/JP2015/078913.

* cited by examiner

IMAGE PICKUP SYSTEM AND IMAGE PROCESSING APPARATUS

CROSS REFERENCE TO RELATED APPLICATION

This application is a continuation application of PCT/JP2015/078913 filed on Oct. 13, 2015 and claims benefit of Japanese Application No. 2014-227183 filed in Japan on Nov. 7, 2014, the entire contents of which are incorporated herein by this reference.

BACKGROUND OF INVENTION

1. Field of the Invention

The present invention relates to an image pickup system and an image processing apparatus, and in particular to an image pickup system and an image processing apparatus for sequentially radiating illumination lights of a plurality of mutually different wavelength bands to perform image pickup of an object.

2. Description of the Related Art

In a medical field, operations using an apparatus which is minimally invasive to a living body, for example, like an endoscope have been conventionally performed.

As an observation method using an endoscope, for example, observation methods such as normal light observation in which an image with coloring almost similar to coloring in observation with naked eyes is obtained by radiating light of each of colors of R (red), G (green) and B (blue) to an object in a living body, and narrowband light observation in which an image in which blood vessels and the like existing on a mucosal surface layer of a living body are emphasized is obtained by radiating light of a band narrower than a band of illumination light for the normal light observation to an object in the living body have been conventionally known.

For example, Japanese Patent No. 4884574 discloses an endoscope system provided with a configuration capable of switching between observation modes corresponding to the normal light observation and narrowband light observation described above.

Further, the endoscope system disclosed in Japanese Patent No. 4884574 is configured as a system which performs such a frame-sequential operation that illumination lights of a plurality of mutually different wavelength bands are sequentially radiated to perform image pickup of an object, and a display image corresponding to one frame is generated with images corresponding to a plurality of fields obtained by performing image pickup of the object.

More specifically, Japanese Patent No. 4884574 discloses, for example, a configuration for, in the narrowband light observation, sequentially radiating narrowband green light nG1, narrowband blue light nB and narrowband blue light nB1 to perform image pickup of an object, performing addition processing of an image obtained in response to radiation of the narrowband blue light nB1 and an image obtained in response to radiation of the narrowband blue light nB to generate a narrowband blue-light image, and displaying a pseudo-color image generated by combining the narrowband blue-light image and an image obtained in response to radiation of the narrowband green light nG1 on a monitor.

SUMMARY OF THE INVENTION

An image pickup system of an aspect of the present invention includes: a light source portion configured to sequentially emit first illumination light with a first wavelength band and second illumination light with a second wavelength band different from the first wavelength band; an image pickup portion configured to perform image pickup of return light from an object illuminated by illumination light emitted from the light source portion for each of predetermined periods and output an image pickup signal; an image generating portion configured to generate a first image corresponding to return light of the first illumination light and a second image corresponding to return light of the second illumination light, each of which corresponds to one field, based on the image pickup signal outputted from the image pickup portion, and sequentially output the first image and the second image; a synchronization processing portion configured to simultaneously output images corresponding to a plurality of fields outputted from the image generating portion, selectively assigning the images to a first channel corresponding to a red color of a display apparatus, a second channel corresponding to a green color of the display apparatus and a third channel corresponding to a blue color of the display apparatus; and a control portion configured to control the synchronization processing portion so as to set image assignment to and image update frequency for the first channel, the second channel and the third channel, respectively, based on one or more evaluation values acquired from the images generated by the image generating portion.

An image processing apparatus of an aspect of the present invention is an image processing apparatus used by being connected to a light source portion configured to sequentially emit first illumination light with a first wavelength band and second illumination light with a second wavelength band different from the first wavelength band, the image processing apparatus including: an image generating portion configured to generate a first image corresponding to return light of the first illumination light and a second image corresponding to return light of the second illumination light, each of which corresponds to one field, based on an image pickup signal outputted from an image pickup portion configured to perform image pickup of return light from an object illuminated by illumination light emitted from the light source portion, and sequentially output the first image and the second image; a synchronization processing portion configured to simultaneously output images corresponding to a plurality of fields outputted from the image generating portion, selectively assigning the images to a first channel corresponding to a red color of a display apparatus, a second channel corresponding to a green color of the display apparatus and a third channel corresponding to a blue color of the display apparatus; and a control portion configured to control the synchronization processing portion so as to set image assignment to and image update frequency for the first channel, the second channel and the third channel, respectively, based on one or more evaluation values acquired from the images generated by the image generating portion.

DETAILED DESCRIPTION OF THE PREFERRED EMBODIMENT(S)

An embodiment of the present invention will be described with reference to the drawings.

FIGS. 1 to 5 relate to the embodiment of the present invention.

Figure 1:
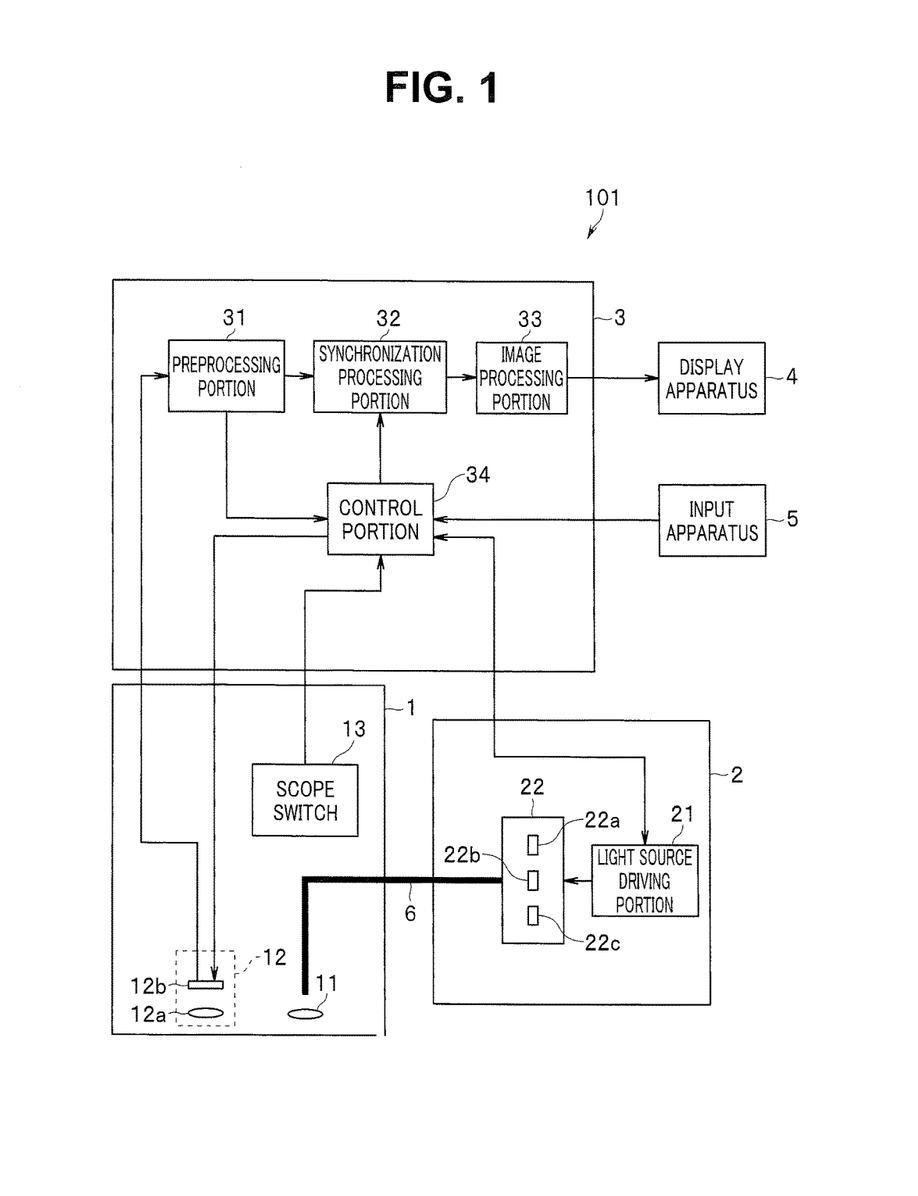
FIG. 1 is a diagram showing a configuration of a main part of an image pickup system according to an embodiment.

As shown in FIG. 1, an image pickup system 101 is provided with: an endoscope 1 provided with an elongated-shaped insertion portion insertable into a subject, which is a living body, and configured to perform image pickup of an object, such as living tissue, in the subject and output an image pickup signal, a light source apparatus 2 configured to supply illumination light used for observation of the object via a light guide 6 insertedly arranged inside the endoscope 1, a processor 3 configured to generate and output a video signal or the like corresponding to the image pickup signal outputted from the endoscope 1, a display apparatus 4 configured to display an image or the like corresponding to the video signal outputted from the processor 3, and an input apparatus 5 provided with switches, buttons and/or the like capable of giving an instruction or the like corresponding to an input operation by a user such as an operator to the processor 3. FIG. 1 is a diagram showing a configuration of a main part of the image pickup system according to the embodiment.

The endoscope 1 is configured being provided at a distal end portion, with an illumination optical system 11 configured to radiate light transmitted by the light guide 6 to an object and an image pickup portion 12 configured to perform image pickup of return light emitted from the object in response to the light radiated from the illumination optical system 11 and output an obtained image pickup signal. Further, the endoscope 1 is configured having a scope switch 13 capable of giving various instructions corresponding to operations by the user to the processor 3.

The image pickup portion 12 is configured to perform image pickup of return light from an object illuminated by illumination light emitted from the light source apparatus 2 and output an image pickup signal. More specifically, the image pickup portion 12 is configured having an objective optical system 12a configured to form an image of return light emitted from an object, and such an image pickup device 12b that an image pickup surface for receiving the return light is arranged being adjusted to an image forming position of the objective optical system 12a.

The image pickup device 12b is provided, for example, with a CCD, and configured to be driven in response to an image pickup device driving signal outputted from the processor 3 and sequentially output image pickup signals obtained by performing image pickup of return light from an object, which is formed on the image pickup surface.

The scope switch 13 is provided, for example, with an observation mode setting switch (not shown) capable of giving an instruction to set an observation mode of the image pickup system 101 to either a white light observation mode or a narrowband light observation mode in response to an operation by the user.

The light source apparatus 2 is configured having a light source driving portion 21 and an LED unit 22.

The light source driving portion 21 is configured being provided, for example, with a driving circuit. Further, the light source driving portion 21 is configured so as to generate and output a light source driving signal for individually causing each LED of the LED unit 22 to emit and extinguish light, based on an illumination control signal outputted from the processor 3.

The LED unit 22 is configured having a red LED 22a, a green LED 22b and a blue LED 22c.

The red LED 22a is configured to emit R light, which is narrowband red light a center wavelength of which is set, for example, to be in a vicinity of 600 nm, based on a light source driving signal outputted from the light source driving portion 21.

The green LED 22b is configured to emit G light, which is narrowband green light a center wavelength of which is set, for example, to be in a vicinity of 540 nm, which is a green area, based on a light source driving signal outputted from the light source driving portion 21.

The blue LED 22c is configured to emit B light, which is narrowband blue light a center wavelength of which is set, for example, to be in a vicinity of 415 nm, which is a blue area, based on a light source driving signal outputted from the light source driving portion 21.

The processor 3 is configured having a preprocessing portion 31, a synchronization processing portion 32, an image processing portion 33 and a control portion 34.

The preprocessing portion 31 is provided with signal processing circuits such as a noise reduction circuit and an A/D conversion circuit and configured to generate image data corresponding to one field by performing processing such as noise reduction and A/D conversion for image pickup signals sequentially outputted from the endoscope 1 and sequentially output the generated image data corresponding to one field to the synchronization processing portion 32 and the control portion 34.

The synchronization processing portion 32 is configured as a synchronization circuit provided, for example, with a selector configured to operate in response to a synchronization processing control signal to be described later and a plurality of memories connected at a rear stage of the selector. Further, the synchronization processing portion 32 is configured to, based on a synchronization processing control signal outputted from the control portion 34, accumulate image data corresponding to a plurality of fields which is sequentially outputted from the preprocessing portion 31 and simultaneously output the accumulated image data corresponding to a plurality of fields to the image processing portion 33, selectively assigning the accumulated image data to an R channel corresponding to a red color of the display apparatus 4, a G channel corresponding to a green color of the display apparatus 4, and a B channel corresponding to a blue color of the display apparatus 4.

The image processing portion 33 is configured being provided, for example, with an image processing circuit such as a combination circuit. Further, the image processing portion 33 is configured to generate image data corresponding to one frame by combining respective image data outputted in a state of being assigned to the R channel, the G channel and the B channel, generate a video signal by performing predetermined image processing such as gamma correction for the generated image data corresponding to one frame, and sequentially output the generated video signal to the display apparatus 4.

The control portion 34 is configured being provided, for example, with a CPU or a control circuit. Further, the control portion 34 is configured to detect an observation mode set by the observation mode setting switch of the scope switch 13, generate an illumination control signal for causing illumination light corresponding to the detected observation mode to be emitted, and output the illumination control signal to the light source driving portion 21. Further, the control portion 34 is configured to generate an image pickup device driving signal for causing an object to be image-picked up, in response to emission of illumination light, and output the image pickup device driving signal to the image pickup device 12b. Further, the control portion 34 is configured to, when detecting that the narrowband light observation mode has been set, generate a synchronization processing control signal for setting each of assignment of image data to the R channel, the G channel and the B channel and image data update frequency, based on a luminance value of image data BD (described later) outputted from the preprocessing portion 31, that is, an evaluation value acquired from the image data BD, and output the synchronization processing control signal to the synchronization processing portion 32.

Next, operation of the image pickup system 101 according to the present embodiment will be described.

First, by operating the observation mode setting switch of the scope switch 13 after connecting each portion of the image pickup system 101 and powering on the image pickup system 101, the user sets the observation mode of the image pickup system 101 to the white light observation mode.

When detecting that the observation mode has been set to the white color observation mode, the control portion 34 generates an illumination control signal for causing R light, G light and B light to be sequentially emitted for each predetermined period FP1 and outputs the illumination control signal to the light source driving portion 21. Further, the control portion 34 generates an image pickup device driving signal for causing return light from an object to be image-picked up for each predetermined period FP1 and outputs the image pickup device driving signal to the image pickup device 12b. Further, when detecting that the observation mode has been set to the white light observation mode, the control portion 34 generates a synchronization processing control signal for setting each of assignment of image data to the R channel, the G channel and the B channel and image data update frequency and outputs the synchronization processing control signal to the synchronization processing portion 32.

The light source driving portion 21 generates and outputs a light source driving signal for causing the respective LEDs of the LED unit 22 to emit light in order of the red LED 22a→green LED 22b→blue LED 22c→red LED 22a→ . . . for each predetermined period FP1, based on the illumination control signal outputted from the control portion 34. According to such an operation of the light source driving portion 21, illumination light emitted from the light source apparatus 2 and radiated to the object via the illumination optical system 11 is switched in order of R light→G light→B light→R light→ . . . for each predetermined period FP1.

The image pickup device 12b picks up an image of the return light from the object illuminated by the illumination light emitted from the light source apparatus 2 and outputs an image pickup signal for each predetermined period FP1, based on the image pickup device driving signal outputted from the control portion 34. That is, according to such an operation of the image pickup device 12b, each of return light received during a period during which R light is radiated, return light received during a period during which G light is radiated and return light received during a period during which B light is radiated is image-picked up once.

The preprocessing portion 31 generates image data RD corresponding to the return light of R light, image data GD corresponding to the return light of G light and image data BD corresponding to the return light of B light, each of which corresponds to one field, based on the image pickup signal outputted from the image pickup device 12b, and sequentially outputs the image data RD, GD and BD to the synchronization processing portion 32 and the control portion 34.

Based on the synchronization processing control signal outputted from the control portion 34, the synchronization processing portion 32 accumulates the image data RD, the image data GD and the image data BD sequentially outputted from the preprocessing portion 31, each of which corresponds to one field, and, furthermore, simultaneously outputs the accumulated image data RD corresponding to one field, the accumulated image data GD corresponding to one field and the accumulated image data BD corresponding to one field to the image processing portion 33, assigning the image data RD, the image data GD and the image data BD to the R channel, the G channel and the B channel, respectively. Further, the synchronization processing portion 32 sequentially performs an operation of updating the image data RD assigned to the R channel once, an operation of updating the image data GD assigned to the G channel once and an operation of updating the image data BD assigned to the B channel once, based on the synchronization processing control signal outputted from the control portion 34.

The image processing portion 33 generates RGB color image data corresponding to one frame by combining the image data RD assigned to the R channel, the image data GD assigned to the G channel and the image data BD assigned to the B channel, generates a video signal by performing predetermined image processing such as gamma correction for the generated RGB color image data corresponding to one frame, and sequentially outputs the video signal to the display apparatus 4.

On the other hand, by inserting the insertion portion of the endoscope 1 into an inside of a subject while checking an image displayed on the display apparatus 4, in a state that the observation mode of the image pickup system 101 is set to the white light observation mode, the user arranges the distal end portion of the insertion portion in a vicinity of a desired object. After that, by operating the observation mode setting switch of the scope switch 13 in the state that the distal end portion of the insertion portion of the endoscope 1 is arranged in the vicinity of the desired object, the user sets the observation mode of the image pickup system 101 to the narrowband light observation mode.

When detecting that the observation mode has been set to the narrowband light observation mode, the control portion 34 generates an illumination control signal for causing G light and B light to be alternately emitted for each predetermined period FP1 and outputs the illumination control signal to the light source driving portion 21. Further, the control portion 34 generates an image pickup device driving signal for causing the return light from the object to be image-picked up for each predetermined period FP1 and outputs the image pickup device driving signal to the image pickup device 12b. Further, when detecting that the observation mode has been set to the narrowband light observation mode, the control portion 34 generates a synchronization processing control signal for setting each of assignment of image data to the R channel, the G channel and the B channel and image data update frequency and outputs the synchronization processing control signal to the synchronization processing portion 32, based on a luminance value of the image data BD outputted from the preprocessing portion 31. Note that the luminance value of the image data BD described above is defined, for example, as an average luminance value of respective pixels included in at least a partial area of the image data BD.

The light source driving portion 21 generates and outputs a light source driving signal for causing the red LED 22a to extinguish light as well as causing the green LED 22b and the blue LED 22c to emit light in order of the green LED 22b→blue LED 22c→green LED 22b→ . . . for each predetermined period FP1, based on the illumination control signal outputted from the control portion 34. According to such an operation of the light source driving portion 21, the illumination light emitted from the light source apparatus 2 and radiated to the object via the illumination optical system 11 is alternately switched in order of G light→B light→G light→ . . . for each predetermined period FP1.

The image pickup device 12b picks up an image of the return light from the object illuminated by the illumination light emitted from the light source apparatus 2 and outputs an image pickup signal for each predetermined period FP1, based on the image pickup device driving signal outputted from the control portion 34. That is, according to such an operation of the image pickup device 12b, each of return light received during the period during which G light is radiated and return light received during the period during which B light is radiated is image-picked up once.

The preprocessing portion 31 generates image data GD corresponding to the return light of G light and image data BD corresponding to the return light of B light, each of which corresponds to one field, based on the image pickup signal outputted from the image pickup device 12b, and sequentially outputs the image data GD and BD to the synchronization processing portion 32 and the control portion 34.

Here, description will be made on an example of an operation performed by the synchronization processing portion 32 when it is detected by the control portion 34 that a luminance value of the image data BD outputted from the preprocessing portion 31 is equal to or above a predetermined threshold TH1.

Based on the synchronization processing control signal outputted from the control portion 34, the synchronization processing portion 32 accumulates the image data GD and the image data BD sequentially outputted from the preprocessing portion 31, each of which corresponds to one field, and, furthermore, simultaneously outputs the accumulated image data GD corresponding to one field and the accumulated image data BD corresponding to one field to the image processing portion 33, assigning the image data GD and the image data BD to the R channel and the G channel, respectively.

Figure 2:
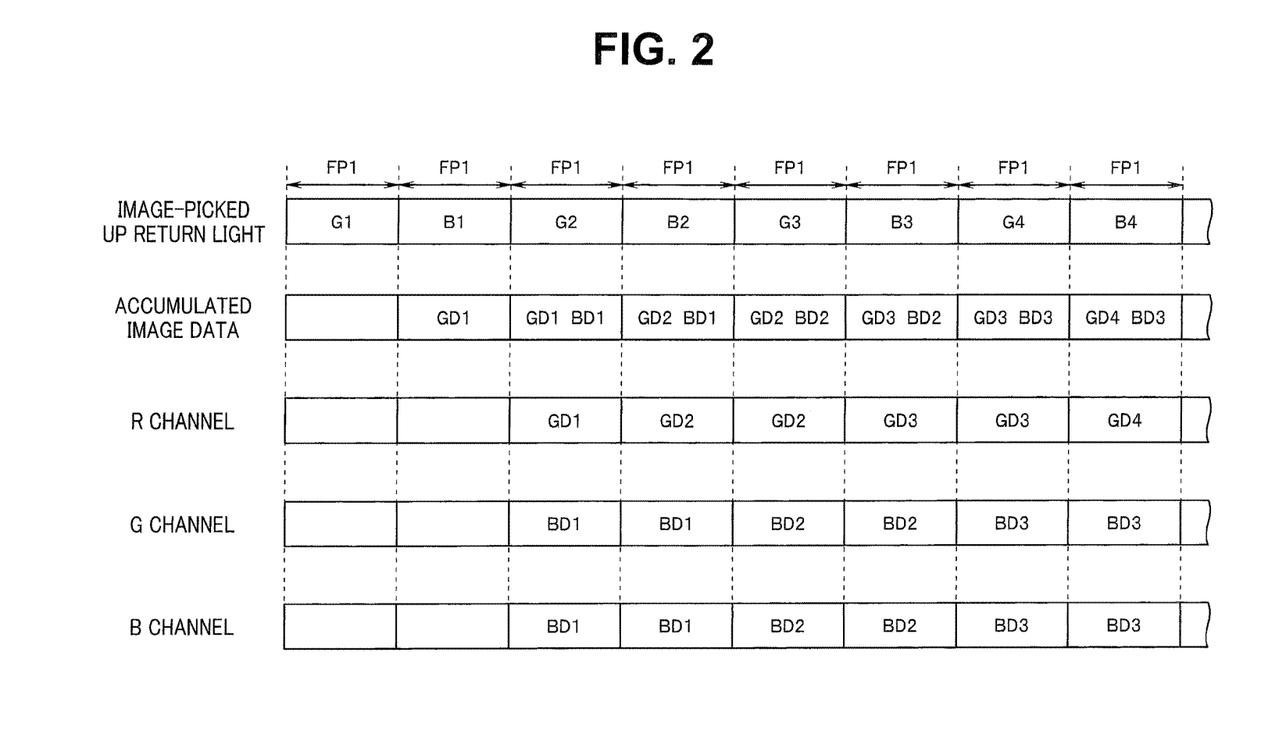
FIG. 2 is a diagram for illustrating an example of operations performed in the image pickup system according to the embodiment.

Further, if the luminance value of the image data BD outputted from the preprocessing portion 31 is equal to or above the predetermined threshold TH1, the synchronization processing portion 32 alternately performs an operation of updating image data (GD1, GD2, GD3, . . . ) assigned to the R channel once and an operation of updating image data (BD1, BD2, BD3, . . . ) assigned to the G channel and the B channel once for each predetermined period FP1 based on the synchronization processing control signal outputted from the control portion 34, for example, as shown in FIG. 2. FIG. 2 is a diagram for illustrating an example of operations performed in the image pickup system according to the embodiment. Note that it is assumed that the operation in FIG. 2 shows an operation in a case where a state that image data has not been accumulated in the synchronization processing portion 32 is a starting point.

That is, when detecting that the luminance value of the image data BD outputted from the preprocessing portion 31 is equal to or above the predetermined threshold TH1, the control portion 34 generates the illumination control signal for causing G light and B light to be alternately emitted for each predetermined period FP1 and outputs the illumination control signal to the light source driving portion 21. Further, when detecting that the luminance value of the image data BD outputted from the preprocessing portion 31 is equal to or above the predetermined threshold TH1, the control portion 34 generates a synchronization processing control signal for causing the image data GD corresponding to one field to be assigned to the R channel, causing the image data BD corresponding to one field to be assigned to each of the G channel and the B channel and, furthermore, causing an operation of updating the image data GD assigned to the R channel once and an operation of updating the image data BD assigned to the G channel and the B channel once to be alternately performed for each predetermined period FP1, and outputs the synchronization processing control signal to the synchronization processing portion 32.

Next, description will be made on an example of an operation performed by the synchronization processing portion 32 when it is detected by the control portion 34 that the luminance value of the image data BD outputted from the preprocessing portion 31 is below the predetermined threshold TH1 and equal to or above a predetermined threshold TH2 (wherein TH2<TH1 is satisfied).

Based on the synchronization processing control signal outputted from the control portion 34, the synchronization processing portion 32 accumulates the image data GD corresponding to one field sequentially outputted from the preprocessing portion 31, accumulates the image data BD corresponding to two temporally adjoining fields sequentially outputted from the preprocessing portion 31, and simultaneously outputs the accumulated image data GD corresponding to one field and image data BDD obtained by doubling a luminance value of image data BDN corresponding to a temporally latter one field between the accumulated pieces of image data BD corresponding to two fields to the image processing portion 33, assigning the image data GD to the R channel and assigning the image data BDD to the G channel and the B channel.

Figure 3:
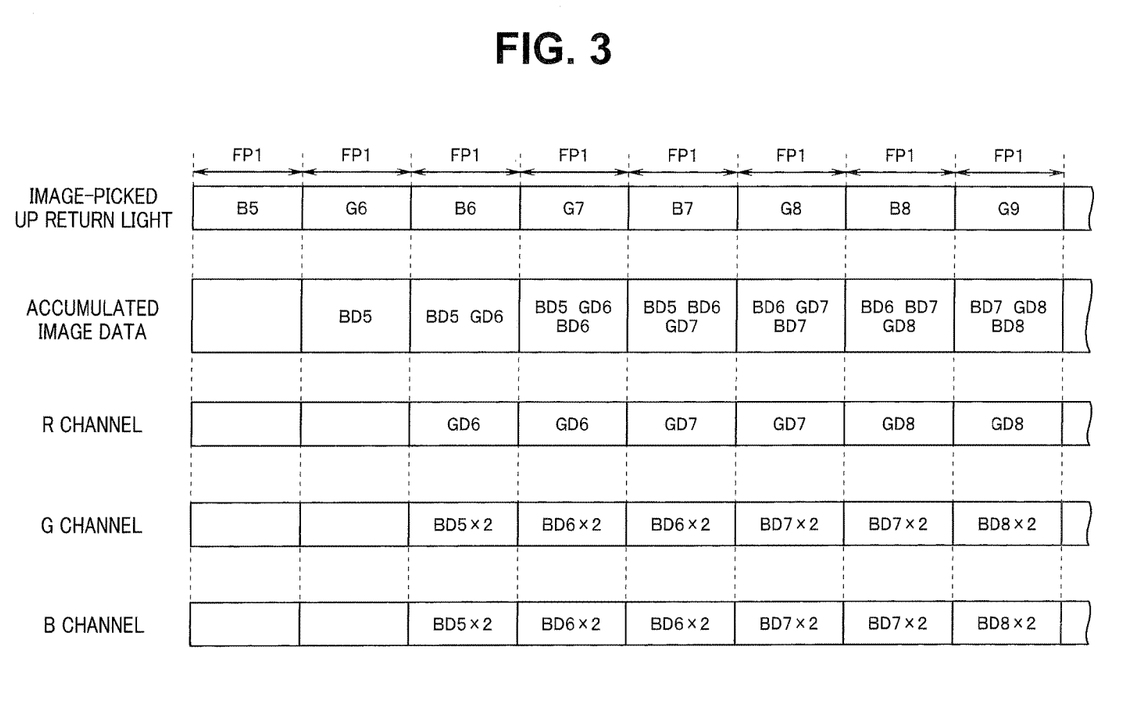
FIG. 3 is a diagram for illustrating an example of the operations performed in the image pickup system according to the embodiment, which is different from FIG. 2.

Further, if the luminance value of the image data BD outputted from the preprocessing portion 31 is below the predetermined threshold TH1, and equal to or below the predetermined threshold TH2, the synchronization processing portion 32 alternately performs an operation of updating image data (GD6, GD7, GD8, . . . ) assigned to the R channel once and an operation of updating image data (BD5×2, BD6×2, BD7×2, . . . ) assigned to the G channel and the B channel once for each predetermined period FP1, for example, as shown in FIG. 3. FIG. 3 is a diagram for illustrating an example of the operations performed in the image pickup system according to the embodiment, which is different from FIG. 2. Note that it is assumed that the operation in FIG. 3 shows an operation in the case where the state that image data has not been accumulated in the synchronization processing portion 32 is the starting point.

That is, when detecting that the luminance value of the image data BD outputted from the preprocessing portion 31 is below the predetermined threshold TH1, and equal to or above the predetermined threshold TH2, the control portion 34 generates the illumination control signal for causing G light and B light to be alternately emitted for each predetermined period FP1 and outputs the illumination control signal to the light source driving portion 21. Further, when detecting that the luminance value of the image data BD outputted from the preprocessing portion 31 is below the predetermined threshold TH1, and equal to or above the predetermined threshold TH2, the control portion 34 generates a synchronization processing control signal for causing the image data GD corresponding to one field to be assigned to the R channel, causing the image data BDD obtained by doubling the luminance value of the image data BD corresponding to one field to be assigned to each of the G channel and the B channel and, furthermore, causing the operation of updating the image data GD assigned to the R channel once and an operation of updating the image data BDD assigned to the G channel and the B channel once to be alternately performed for each predetermined period FP1, and outputs the synchronization processing control signal to the synchronization processing portion 32.

Next, description will be made on an example of operations performed by the synchronization processing portion 32 when it is detected by the control portion 34 that the luminance value of the image data BD outputted from the preprocessing portion 31 is below the predetermined threshold TH2.

Based on the synchronization processing control signal outputted from the control portion 34, the synchronization processing portion 32 accumulates the image data GD corresponding to one field sequentially outputted from the preprocessing portion 31, accumulates the image data BD corresponding to two temporally adjoining fields sequentially outputted from the preprocessing portion 31, and simultaneously outputs the accumulated image data GD corresponding to one field and image data BDS obtained by adding the luminance values of the accumulated image data BD corresponding to two fields to the image processing portion 33, assigning the image data GD to the R channel and assigning the image data BDS to the G channel and the B channel.

Figure 4:
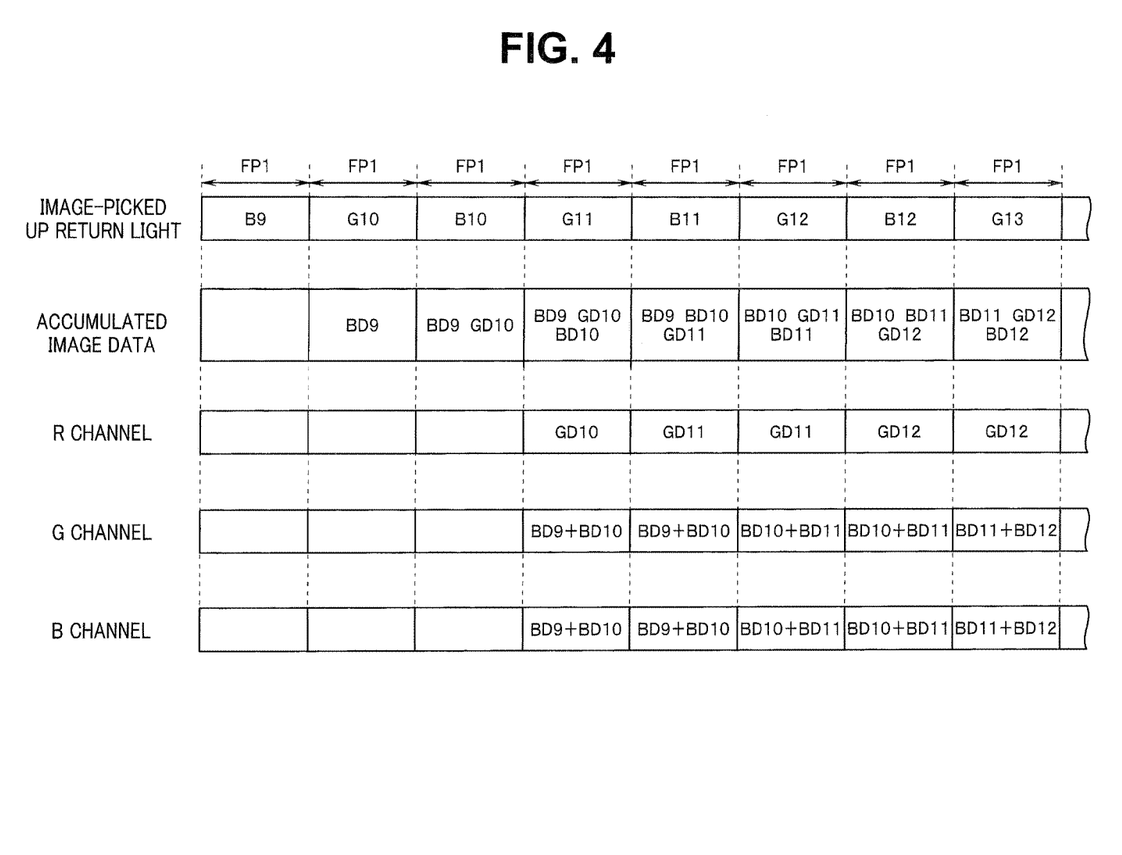
FIG. 4 is a diagram for illustrating an example of the operations performed in the image pickup system according to the embodiment, which is different from FIGS. 2 and 3.

Further, if the luminance value of the image data BD outputted from the preprocessing portion 31 is below the predetermined threshold TH2, the synchronization processing portion 32 alternately performs an operation of updating image data (GD10, GD11, GD12, . . . ) assigned to the R channel once and an operation of updating image data (BD9+BD10, BD10+BD11, BD11+BD12, . . . ) assigned to the G channel and the B channel once for each predetermined period FP1, for example, as shown in FIG. 4. FIG. 4 is a diagram for illustrating an example of the operations performed in the image pickup system according to the embodiment, which is different from FIGS. 2 and 3. Note that it is assumed that the operation in FIG. 4 shows an operation in the case where the state that image data has not been accumulated in the synchronization processing portion 32 is the starting point.

That is, when detecting that the luminance value of the image data BD outputted from the preprocessing portion 31 is below the predetermined threshold TH2, the control portion 34 generates the illumination control signal for causing G light and B light to be alternately emitted for each predetermined period FP1 and outputs the illumination control signal to the light source driving portion 21. Further, when detecting that the luminance value of the image data BD outputted from the preprocessing portion 31 is below the predetermined threshold TH2, the control portion 34 generates a synchronization processing control signal for causing the image data GD corresponding to one field to be assigned to the R channel, causing the image data BDS obtained by adding the luminance values of the image data BD corresponding to two temporally adjoining fields to be assigned to each of the G channel and the B channel and, furthermore, causing the operation of updating the image data GD assigned to the R channel once and an operation of updating the image data BDS assigned to the G channel and the B channel once to be alternately performed for each predetermined period FP1, and outputs the synchronization processing control signal to the synchronization processing portion 32.

The image processing portion 33 generates pseudo color image data corresponding to one frame by combining the image data GD assigned to the R channel and the image data BD, BDD or BDS assigned to the G channel and the B channel, generates a video signal by performing predetermined image processing such as gamma correction for the generated pseudo color image data corresponding to one frame, and sequentially outputs the video signal to the display apparatus 4.

Note that the control portion 34 of the present embodiment is not limited to such that is configured to acquire the luminance value of the image data BD outputted from the preprocessing portion 31 as an evaluation value and generate a synchronization processing control signal in the narrowband light observation mode but may be, for example, such that is configured to acquire a noise amount obtained by quantifying magnitude of noise included in the image data BD outputted from the preprocessing portion 31 as the evaluation value and generate the synchronization processing control signal. More specifically, the control portion 34 may be, for example, such that is configured to generate a synchronization processing control signal for causing an operation as shown in FIG. 2 to be performed when detecting that a noise amount of the image data BD outputted from the preprocessing portion 31 is below a predetermined threshold TN1, generate a synchronization processing control signal for causing an operation as shown in FIG. 3 to be performed when detecting that the noise amount is equal to or above the predetermined threshold TN1 and below TN2 (wherein TN2>TN1 is satisfied) and generate a synchronization processing control signal for causing an operation as shown in FIG. 4 to be performed when detecting that the noise amount is equal to or above the threshold TN2.

Further, the control portion 34 of the present embodiment is not limited to such that is configured to acquire the luminance value of the image data BD outputted from the preprocessing portion 31 as an evaluation value and generate a synchronization processing control signal in the narrowband light observation mode but may be, for example, such that is configured to acquire at least either the luminance value of the image data BD or the luminance value of the image data GD outputted from the preprocessing portion 31 as the evaluation value and generate the synchronization processing control signal.

On the other hand, in the present embodiment, for example, when the luminance value of the image data BD outputted from the preprocessing portion 31 is below the predetermined threshold TH2 in the narrowband light observation mode, an operation as described below may be performed.

When detecting that the luminance value of the image data BD outputted from the preprocessing portion 31 is below the predetermined threshold TH2 in the narrowband light observation mode, the control portion 34 generates an illumination control signal for causing an operation of emitting G light once during one predetermined period FP1 and an operation of emitting B light once during each of two predetermined periods FP1 to be alternately performed, and outputs the illumination control signal to the light source driving portion 21. Further, the control portion 34 generates an image pickup device driving signal for causing the return light from the object to be image-picked up for each predetermined period FP1 and outputs the image pickup device driving signal to the image pickup device 12b. Further, when the luminance value of the image data BD outputted from the preprocessing portion 31 is below the predetermined threshold TH2, the control portion 34 generates a synchronization processing control signal for setting image data to be assigned to the R channel, the G channel and the B channel and outputs the synchronization processing control signal to the synchronization processing portion 32.

The light source driving portion 21 generates and outputs a light source driving signal for causing the red LED 22a to extinguish light as well as causing the green LED 22b and the blue LED 22c to emit light once in order of the green LED 22b→blue LED 22c→blue LED 22c→green LED 22b→blue LED 22c→blue LED 22c→green LED 22b→ . . . for each predetermined period FP1, based on the illumination control signal outputted from the control portion 34. According to such an operation of the light source driving portion 21, illumination light emitted from the light source apparatus 2 and radiated to the object via the illumination optical system 11 is switched in order of G light→B light→B light→G light→B light→B light→G light→ . . . for each predetermined period FP1.

The image pickup device 12b picks up an image of the return light from the object and outputs an image pickup signal for each predetermined period FP1, based on the image pickup device driving signal outputted from the control portion 34. That is, according such an operation of the image pickup device 12b, return light received during the period during which G light is radiated is image-picked up once, and return light received during the period during which B light is radiated is image-picked up twice.

The preprocessing portion 31 generates image data GD corresponding to the return light of G light and image data BD corresponding to the return light of B light, each of which corresponds to one field, based on the image pickup signal outputted from the image pickup device 12b, and sequentially outputs the image data GD and the image data BD to the synchronization processing portion 32 and the control portion 34.

Based on the synchronization processing control signal outputted from the control portion 34, the synchronization processing portion 32 accumulates the image data GD corresponding to one field sequentially outputted from the preprocessing portion 31, accumulates the image data BD corresponding to two temporally adjoining fields sequentially outputted from the preprocessing portion 31, and simultaneously outputs the accumulated image data GD corresponding to one field and image data BDT obtained by adding the luminance values of the accumulated image data BD corresponding to two fields to the image processing portion 33, assigning the image data GD to the R channel and assigning the image data BDT to the G channel and the B channel.

Figure 5:
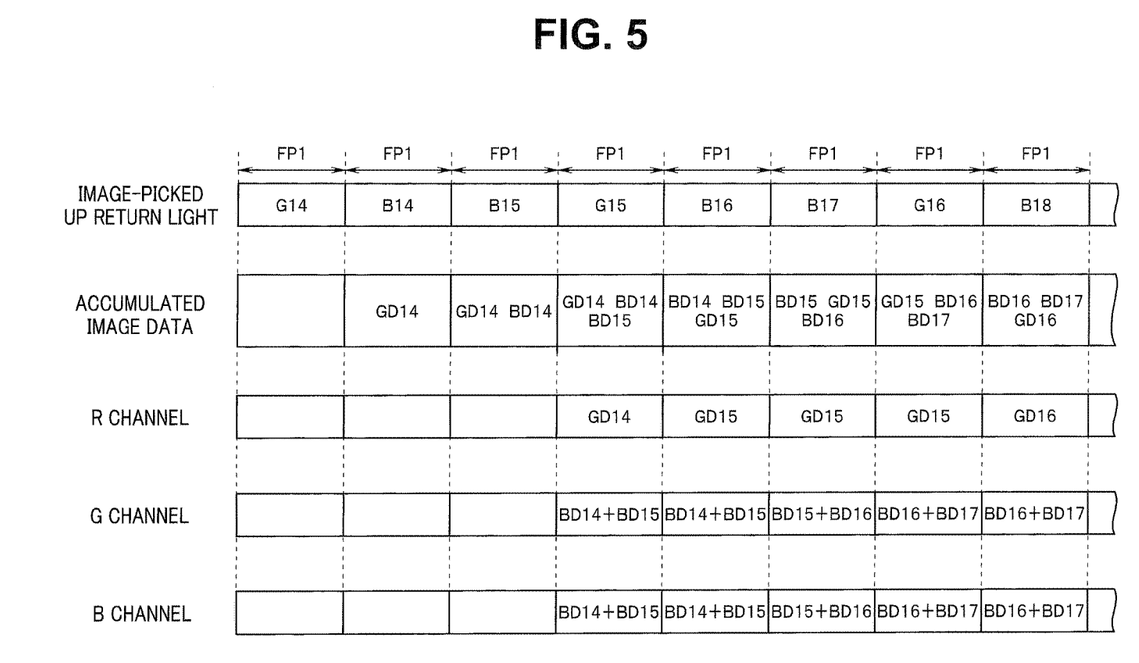
FIG. 5 is a diagram for illustrating an example of the operations performed in the image pickup system according to the embodiment, which is different from FIGS. 2 to 4.

Further, based on the synchronization processing control signal outputted from the control portion 34, the synchronization processing portion 32 alternately performs an operation of updating image data (GD14, GD15, GD16) assigned to the R channel once and an operation of updating image data (BD14+BD15, BD15+BD16, BD16+BD17, . . . ) assigned to the G channel and the B channel twice consecutively, for example, as shown in FIG. 5. FIG. 5 is a diagram for illustrating an example of the operations performed in the image pickup system according to the embodiment, which is different from FIGS. 2 to 4. Note that it is assumed that the operation in FIG. 5 shows an operation in the case where the state that image data has not been accumulated in the synchronization processing portion 32 is the starting point.

As described above, according to the present embodiment, an operation of making adjustments between a timing of alternately radiating G light and B light to perform image pickup of an object in the narrowband light observation mode and a timing of updating a combination of image data assigned to the R, G and B channels is performed. Therefore, it is possible to prevent occurrence of frame dropping in video displayed on the display apparatus 4. Therefore, according to the present embodiment, it is possible to improve image quality of video displayed in frame-sequential narrowband light observation.

Note that, according to the present embodiment, the input apparatus 5 may be provided, for example, with a switch capable of giving an instruction for setting the operation of the synchronization processing portion 32 performed when the luminance value of the image data BD outputted from the preprocessing portion 31 is below the predetermined threshold TH1 to one of the operations shown in FIGS. 3 and 4 to the processor 3.

Note that the present invention is not limited to each embodiment described above, and it is, of course, possible to make various changes and applications within a range not departing from the spirit of the invention.

What is claimed is:

1. An image pickup system comprising:
   a light source portion configured to sequentially emit first illumination light with a first wavelength band and second illumination light with a second wavelength band different from the first wavelength band;
   an image pickup portion configured to perform image pickup of return light from an object illuminated by illumination light emitted from the light source portion for each of predetermined periods and output an image pickup signal;
   an image generating portion configured to generate a first image corresponding to return light of the first illumination light and a second image corresponding to return light of the second illumination light, each of which corresponds to one field, based on the image pickup signal outputted from the image pickup portion, and sequentially output the first image and the second image;
   a synchronization processing portion configured to simultaneously output images corresponding to a plurality of fields outputted from the image generating portion, selectively assigning the images to a first channel corresponding to a red color of a display apparatus, a second channel corresponding to a green color of the display apparatus and a third channel corresponding to a blue color of the display apparatus; and
   a control portion configured to control the synchronization processing portion so as to set image assignment to and image update frequency for the first channel, the second channel and the third channel, respectively, based on one or more evaluation values acquired from the images generated by the image generating portion.

2. The image pickup system according to claim 1, wherein the control portion further controls the synchronization processing portion so as to set image update frequency for the first channel, the second channel and the third channel, based on the evaluation values acquired from the images generated by the image generating portion.

3. The image pickup system according to claim 1, wherein each of the evaluation values is either a luminance value of each of the images generated by the image generating portion or a noise amount obtained by quantifying a magnitude of noise included in each of the images generated by the image generating portion.

4. The image pickup system according to claim 3, wherein the control portion controls the light source portion to alternately emit the first illumination light and the second illumination light for each of the predetermined periods when detecting that the luminance value is equal to or above a predetermined threshold TH1 or when detecting that the noise amount is below a predetermined threshold TN1, and controls the synchronization processing portion to assign the first image corresponding to one field to the first channel, assign the second image corresponding to one field to each of the second channel and the third channel and, furthermore, alternately perform an operation of updating the first image assigned to the first channel once and an operation of updating the second image assigned to the second channel and the third channel once for each of the predetermined periods.

5. The image pickup system according to claim 3, wherein the control portion controls the light source portion to alternately emit the first illumination light and the second illumination light for each of the predetermined periods when detecting that the luminance value is below a predetermined threshold TH1 and equal to or above a predetermined threshold TH2 or when detecting that the noise amount is equal to or above a predetermined threshold TN1 and below a predetermined threshold TN2, and controls the synchronization processing portion to assign the first image corresponding to one field to the first channel, assign a third image obtained by doubling the luminance value of the second image corresponding to one field to each of the second channel and the third channel and, furthermore, alternately perform the operation of updating the first image assigned to the first channel once and an operation of updating the third image assigned to the second channel and the third channel once for each of the predetermined periods.

6. The image pickup system according to claim 3, wherein the control portion controls the light source portion to alternately emit the first illumination light and the second illumination light for each of the predetermined periods when detecting that the luminance value is below a predetermined threshold TH2 or when detecting that the noise amount is equal to or above a predetermined threshold TN2, and controls the synchronization processing portion to assign the first image corresponding to one field to the first channel, assign a fourth image obtained by adding the luminance value in plurality of the second image in plurality corresponding to two temporally adjoining fields to each of the second channel and the third channel and, furthermore, alternately perform the operation of updating the first image assigned to the first channel once and an operation of updating the fourth image assigned to the second channel and the third channel once for each of the predetermined periods.

7. The image pickup system according to claim 3, wherein the control portion controls the light source portion to alternately perform an operation of emitting the first illumination light once during one of the predetermined periods and an operation of emitting the second illumination light once during each of two of the predetermined periods when detecting that the luminance value is below a predetermined threshold TH2 or when detecting that the noise amount is equal to or above a predetermined threshold TN2, and controls the synchronization processing portion to assign the first image corresponding to one field to the first channel, assign a fourth image obtained by adding the luminance value in plurality of the second image in plurality corresponding to two temporally adjoining fields to each of the second channel and the third channel and, furthermore, alternately perform the operation of updating the first image assigned to the first channel once and an operation of updating the fourth image assigned to the second channel and the third channel twice consecutively.

8. The image pickup system according to claim 1, further comprising an image processing portion configured to generate an image corresponding to one frame by combining the respective images outputted from the synchronization processing portion in a state of being assigned to the first channel, the second channel and the third channel, and sequentially output the generated image to the display apparatus.

9. An image processing apparatus used by being connected to a light source portion configured to sequentially emit first illumination light with a first wavelength band and second illumination light with a second wavelength band different from the first wavelength band, the image processing apparatus comprising:
an image generating portion configured to generate a first image corresponding to return light of the first illumination light and a second image corresponding to return light of the second illumination light, each of which corresponds to one field, based on an image pickup signal outputted from an image pickup portion configured to perform image pickup of return light from an object illuminated by illumination light emitted from the light source portion, and sequentially output the first image and the second image;
a synchronization processing portion configured to simultaneously output images corresponding to a plurality of fields outputted from the image generating portion, selectively assigning the images to a first channel corresponding to a red color of a display apparatus, a second channel corresponding to a green color of the display apparatus and a third channel corresponding to a blue color of the display apparatus; and
a control portion configured to control the synchronization processing portion so as to set image assignment to and image update frequency for the first channel, the second channel and the third channel, respectively, based on one or more evaluation values acquired from the images generated by the image generating portion.

* * * * *